United States Patent [19]
Naumann et al.

[11] 3,978,206
[45] Aug. 31, 1976

[54] DENTAL COMPOSITIONS AND APPLIANCES CONTAINING ANTI-CARIOUS ION EXCHANGE RESINS

[75] Inventors: Günther Naumann, Leverkusen; Gustav Pieper, Cologne-Stammheim; Hans-Joachim Rehberg, Leverkusen, all of Germany

[73] Assignee: Bayer Aktiengesellschaft, Leverkusen, Germany

[22] Filed: Aug. 9, 1971

[21] Appl. No.: 170,319

[30] Foreign Application Priority Data

Nov. 6, 1968 Germany .......................... 1807299

[52] U.S. Cl. .................................. 424/49; 424/52; 424/57; 424/79

[51] Int. Cl.$^2$ .................................. A61K 7/18

[58] Field of Search .................... 424/79, 52, 57; 260/2.1 R, 2.2 R; 210/62

[56] References Cited

UNITED STATES PATENTS 3,425,790 2/1969 Sloan .................................. 210/62

OTHER PUBLICATIONS

Calmon et al., Ion Exchangers in Organic and Biochemistry, published by Interscience Publishers, Inc., New York, 1957, p. 3.

*Primary Examiner*—Shep K. Rose

[57] ABSTRACT

Tooth pastes, tooth filling and repair materials, tooth lacquers, dental prostheses and other products and appliances coming into contact with live teeth and tooth surfaces are rendered anti-carious by incorporating therein ion exchange resins containing fluorine, phosphate or calcium ions.

7 Claims, No Drawings

DENTAL COMPOSITIONS AND APPLIANCES CONTAINING ANTI-CARIOUS ION EXCHANGE RESINS

It is generally accepted that dental caries are ascribable to certain microorganisms which form lactic acid in the mouth from carbohydrates that are ingested, the lactic acid acting by dissolving or attacking the calcium phosphates of the tooth substance. Attempts have, therefore, been made to render this lactic acid harmless or to offset its formation by calcium carbonate or other alkaline substances capable of neutralizing acids, but without achieving the desired result.

It is also known that the development of caries can be somewhat inhibited or restricted by increasing the concentration of certain ions, especially fluorine, phosphate or calcium ions. Therefore, for example, in some supply districts drinking water containing too few fluorine ions has been artifically enriched with fluorides, or fluorine compounds have been added to tooth pastes in order to transform, more or less completely, either internally or locally the calcium phosphates (hydroxy apatite) of the tooth substance into fluorine compounds or derivatives which are extremely difficult to dissolve. On the other hand, the possibility has been utilized of decreasing the solubility of the hydroxy apatite and the other calcium phosphates by increasing the concentration of the calcium or phosphate ions in the salivary liquid. However, the usually used calcium compounds such as calcium carbonate or phosphate, serving primarily as cleaning or abrasive agents, cannot be used for the production of fluoride-containing tooth pastes since they are converted by fluorine ions into insoluble calcium fluoride so that no fluorine ions are available for the protection of the teeth. Therefore, other abrasive agents, such as powders of synthetic materials, have been used in these cases.

It has now been found in accordance with the present invention that tooth pastes, dental devices, such as prostheses and jaw-orthopedic appliances, tooth-filling and repair compositions, tooth lacquers, and other products and appliances which come into contact with live teeth, can be made to inhibit caries-susceptibility when they contain ion exchange resins which are charged with caries-inhibiting ions.

Ion exchange resins to be used for this purpose are the per se known products, as for example, cross-linked copolymers substituted by basic or acidic groups and obtained from styrene and divinyl benzene. The total caries-inhibiting amount of ions available after charging them into the ion exchange resins depends upon the capacity of the resin and the speed or rate of the discharge; the degree of dissociation of the polymeric salt. It is possible in some cases, as where calcium salts of strongly acidic cation exchangers are used, to achieve a depositing effect with a gradual discharge of the calcium. It is advantageous to use a resin which, in the charged state, gives off an amount of ions as small as possible to distilled water so that the caries-inhibiting ions are liberated in the mouth liquid only by exchange processes.

A locally restricted, but very long lasting protection against caries can be achieved when the charged ion exchange resins are incorporated into the usual dental synthetic materials when producing fillings, prostheses, jaw-orthopedic appliances, lacquers, etc. Due to the slow water exchange penetrating the synthetic material, the protective ions are discharged only very gradually, but they become effective at those places which, according to experience, are especially susceptible to a renewed occurrence of caries. This is true, for example, for the cavity walls of fillings or for tooth surfaces to which a prosthesis or a jaw-orthopedic appliance is contiguous.

The resins are to be used in comminuted form. A particle size of $<100\ \mu$ will generally be advantageous since, in this case, the mechanical cleaning effect of tooth pastes is greatest and also because a substantial impairment of the mechanical properties is not to be expected. The amount of the addition of ion exchange resin to the tooth paste or to the synthetic compositions may vary within wide limits. In general, about 10 percent additive will be required for tooth pastes, and about 5 percent for the synthetic compositions.

The extent of activity of the ion exchangers to be used according to the invention can be shown by means of a model experiment by comparing their reaction toward distilled and salt-containing water. As a model of the saliva liquid a solution of 50 mg of sodium chloride and 100 g/mg of potassium chloride per 100 ml water is used, a solution which, with regard to its composition of mineral substances, approximately corresponds to human saliva. For the experiments (A) to (C) of the following Table, portions of 10g each of the ion exchange resin were mixed with 1 liter of distilled water or with the "model saliva" on the rolling bench and the liquid was separated after one hour (1st extract). The 2nd and 3rd extracts were obtained by repeating the experiment. The liberated ions in the separated liquids were determined according to customary procedures.

Table

| Ion exchanger | charged with | discharge of dist. water 1st extr. | 2nd extr. | 3rd extr. | discharge of the "model saliva" 1st extr. | 2nd extr. | 3rd extr. |
|---|---|---|---|---|---|---|---|
| (A) | 610 mg | 180 mg | 20 mg | 14 mg | 400 mg | — | — |
| | F | 29.5% | 3.3 % | 2.3 % | 65 % | | |
| (B) | 730 g | 153 mg | 37 mg | 37 mg | 730 mg | — | — |
| | $PO_4$ | 21 % | 5 % | 5 % | 100 % | | |
| (C) | 880 mg | 0 | 0 | 0 | 90 mg | 48 mg | 40 mg |
| | Ca | — | — | — | 10 % | 5.5 % | 4.5 % |

Ion Exchanger (A)

The anion exchanger charged with fluorine ions was prepared by the reaction of a strongly basic ion exchange resin in the hydroxyl form with an aqueous sodium fluoride solution and contained, after rinsing with water, 6.1% fluorine on a dry basis.

Ion Exchanger (B)

In an analogous manner, the anion exchanger charged with phosphate ions was obtained by treatment with orthophosphoric acid. After rinsing, it contained 7.3% $PO_4$ on a dry basis.

Ion Exchanger (C)

From a strongly acidic cation exchanger present in the form of the free acid, there was obtained, by treatment with an aqueous calcium chloride solution, the calcium ion-charged form with 8.8% calcium on a dry basis.

EXAMPLE

Into a mixture consisting of monomeric and polymeric methacrylic acid methyl ester commercially available for the production of dental prostheses material there were incorporated, with the addition of the conventional polymerization catalysts, 5% of the anion exchanger (A) charged with fluorine ions and the mixture was then molded to give a plate weighing 6.57g. This plate then contained 20 mg of fluorine ions. It was placed at 40°C in 500 ml of the model saliva. After 24 hours, 2.7 mg of fluorine or 13.5% of the total amount had entered the solution. The fluorine concentration in the solution remained constant for 14 days. When the solution was renewed after the first day, a further 1.7 mg of fluorine (8.5% of the total amount) had entered the solution under otherwise the same conditions.

In similar manner, tests were carried out with ion exchangers (B) and (C).

What is claimed is:

1. In a dental composition a minor amount effective to inhibit caries of an ion exchange resin containing, as part of the exchangeable ions thereof, an anti-carious agent selected from the group consisting of fluoride, phosphate and calcium ions.

2. A composition according to claim 1 in which the ion exchange resin has a particle size of less than 100 microns.

3. A composition according to claim 1 in which the ion exchange resin is present in the formulation in the amount of approximately 5 to 10% by weight.

4. A composition according to claim 1 in which the anti-carious agent is fluoride ion in the amount of about 6.1%, calculated on a dry basis of the ion exchange resin.

5. A composition according to claim 1 in which the anti-carious agent is phosphate ion in the amount of 7.3%, calculated on a dry basis of the ion exchange resin.

6. A composition according to claim 1 in which the anti-carious agent is calcium ion in the amount of about 8.8% Ca, calculated on a dry basis of the ion exchange resin.

7. In a tooth filling and repair material, a minor amount effective to inhibit caries of an ion exchange resin containing, as part of the exchangeable ions thereof, an anti-carious agent selected from the group consisting of fluoride, phosphate and calcium ions.

* * * * *